United States Patent [19]

Devlin et al.

[11] Patent Number: 4,692,448
[45] Date of Patent: Sep. 8, 1987

[54] BIS(ARYLPIPERAZINYL)SULFUR COMPOUNDS

[75] Inventors: John P. Devlin, Sharon; Karl D. Hargrave, Brookfield Center, both of Conn.

[73] Assignee: Boehringer Ingelheim Pharmaceuticals, Inc., Ridgefield, Conn.

[21] Appl. No.: 673,474

[22] Filed: Nov. 20, 1984

[51] Int. Cl.$^4$ .................... A61K 31/495; C07D 403/12
[52] U.S. Cl. ...................................... 514/252; 544/357
[58] Field of Search .......................... 544/357; 514/252

[56] References Cited

U.S. PATENT DOCUMENTS 2,948,727  8/1960  D'Amico ............................. 544/357
3,138,597  6/1964  Schut ................................. 544/377

FOREIGN PATENT DOCUMENTS 1285476  12/1968  Fed. Rep. of Germany ...... 544/357
 661537  11/1951  United Kingdom ................ 544/357
1246127   9/1971  United Kingdom ................ 544/357

OTHER PUBLICATIONS

Nakanishi et al., *Chemical Abstracts*, vol. 70, (1969), Entry 1172F.

*Primary Examiner*—Donald G. Daus
*Assistant Examiner*—William A. Teoli, Jr.
*Attorney, Agent, or Firm*—David E. Frankhouser; Alan R. Stempel

[57] ABSTRACT

Disclosed are novel bis(arylpiperazinyl)sulfur compounds represented by formula I

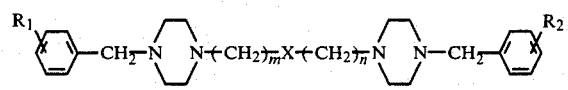

wherein: $R_1$ and $R_2$ are each independently hydrogen, lower alkyl, halogen, nitrile or methylthio; m and n are each independently 2 or 3; and X is a dithio, thio, sulfinyl or sulfonyl and nontoxic, pharmaceutically acceptable addition salts thereof. These compounds can be used for the prevention of allergic disorders, such as asthma, rhinitis, conjunctivitis, hay fever, urticaria, food allergies, and the like.

18 Claims, No Drawings

BIS(ARYLPIPERAZINYL)SULFUR COMPOUNDS

BACKGROUND OF THE INVENTION

1. Field of the Invention

The present invention relates generally to the field of immunology, in particular allergy, and inflammation and compounds effective to modify the operation of such systems and functions. More particularly, it relates to compounds, their preparation and use in the prevention or amelioration of allergic or inflammatory disorders.

2. Brief Description of the Prior Art

Several factors are important in the production of the atopic state of allergic individuals. These factors include the predisposition to produce high levels of IgE against certain antigens and altered sensitivity to the humoral mediators of allergy. Some atopic individuals produce a sustained IgE response when exposed to certain antigens called allergens. The most typical clinical result of antiallergen IgE production is allergy. Allergy is a consequence of the binding of IgE to basophils and mast cells. The combination of allergens with cytophilic IgE leads to cellular degranulation and release of histamine as well as other mediators of the allergic response. See Thaler, et al, *Medical Immunology*, J. B. Lippincott Co., Philadelphia (1977).

The specific blocking of the histamine ($H_1$) receptor by certain drugs, the antihistamines, is the basis for their therapeutic efficacy in preventing and treating allergic manifestations of immediate-type hypersensitivity.

Therapy aimed at controlling the symptoms of immediate hypersensitivity reactions with antihistamines is useful but only partially effective. An attractive and advantageous procedure, uniquely applicable to prophylaxis, is to prevent production or release of mediators, such as histamine, by inhibiting responses of sensitized mast cells and basophils to specific antigens. Adrenergic drugs and theophylline, beside their many other other actions, tend to inhibit such allergic responses. This may contribute to the clinical utility. A much more specific inhibition can be achieved, however, with the type of antiallergic drug exemplified by cromolyn sodium. This agent inhibits antigen-induced secretion of histamine from human pulmonary mast cells and from mast cells at certain other sites. Although, the drug is a valuable adjunct in the prophylactic management of certain cases of asthma and certain other atopic states, the usefulness of cromolyn is circumscribed since human basophils, curiously, are not protected. Goodman and Gilman (Eds.), *Pharmacological Basis of Therapeutics*, 6th Ed, MacMillan Publishing Co., Inc., N.Y. (1980).

SUMMARY OF THE INVENTION

This invention relates to novel bis(arylpiperazinyl) sulfur compounds and nontoxic addition salts thereof, to methods of preparing these compounds, to pharmaceutical compositions containing them as active ingredients, and to methods of using them in indications wherein the inhibition of mediator release from various cell systems is beneficial.

More particularly, the present invention relates to novel bis(arylpiperazinyl) sulfur compounds represented by formula I

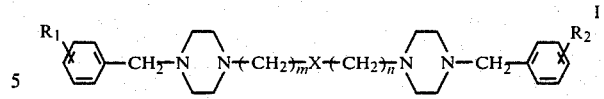

wherein: $R_1$ and $R_2$ are each independently hydrogen, lower alkyl, halogen, particularly chlorine or bromine, nitrile or methylthio; m and n are each independently 2 or 3; and X is dithio, thio, sulfinyl or sulfonyl and nontoxic, pharmaceutically acceptable addition salts thereof.

In subgeneric aspects, the invention comprehends the following classes of compounds, or a nontoxic, pharmaceutically acceptable addition salt thereof:

A. A compound of formula I wherein $R_1$ and $R_2$ are both in the para position; m and n are defined above; and X is a thio or dithio, and pharmaceutically acceptable addition salts thereof.

B. A compound of formula I wherein $R_1$ and $R_2$ are both in the para position; m and n are as defined above and X is a sulfonyl or sulfinyl, and non toxic, pharmaceutically acceptable addition salts thereof.

C. Particularly preferred is a compound of formula I wherein $R_1$ and $R_2$ are each a chlorine in the para position; m and n are each 2; and X is a dithio, e.g. 1,1'-(Dithiodi-2,1-ethanediyl)bis [4-(4-chlorobenzyl)piperazine] and nontoxic, pharmaceutically acceptable addition salts thereof.

The compounds of formula I are capable of inhibiting in vitro the immunological (IgE-mediated) and nonimmunological release of histamine from human peripheral blood leukocytes (basophils), and are useful in warm blooded animals for inhibiting the antigen-induced cellular release of histamine and/or other mediators of the allergic reaction. These compounds, particularly 1,1'-(Dithiodi-2,1-ethanediyl)bis[4-(4-chlorobenzyl)piperazine], are also effective in blocking the metabolic conversion of arachidonic acid in the lipoxygenase pathway. Further, the compounds of the invention are particularly advantageous in that they exhibit little cytolytic effect on the cells with which they interact, e.g., basophils, etc., up to the solubility limits of the compounds and thus avoid this undesirable potential cause of mediator release.

The compounds of formula I can be used for the prevention of allergic disorders, such as asthma, rhinitis, conjunctivitis, hay fever, urticaria, food allergies, and the like. By virtue of their ability to inhibit cellular mediator release, the compounds may also be useful for the prevention of inflammatory or immunological disorders.

DETAILED DESCRIPTION OF THE PREFERRED EMBODIMENTS

Although specific terms are used in the following description for clarity, they refer only to the particular embodiment(s) selected for illustration, and are not intended to limit the scope of the invention.

The compounds of the present invention can be prepared by several methods, selected ones of which are described below. The starting materials used in the examples are commercially available or can be synthesized by well known published procedures from commer- cially available materials unless otherwise fully described here. Standard reagent grade chemicals are used in these preparations and in the working examples which follow unless otherwise specifically indicated.

Compounds of formula I in which X is a dithio linkage can be made in one method, wherein a compound of formula II:

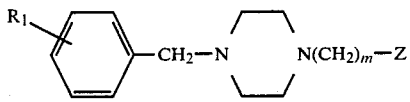

wherein $R_1$ and m can have the meanings defined above, and Z can be a good leaving group such as halogen, tosyl, sulfuric acid ester or sulfonic acid ester is treated with thiourea to form an isothiouronium halide of formula III:

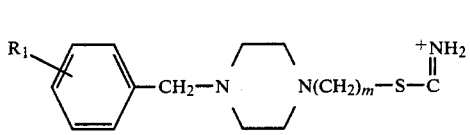

This reaction can be carried out in known manner in an inert organic solvent such as ethanol, dimethylformamide or dimethylsulfoxide, optionally in the present of a base such as triethylamine, at temperatures from about ambient up to the reflux temperature of the solvent. The isothiouronium halide so-formed is then hydrolyzed to produce a thiol of formula IV:

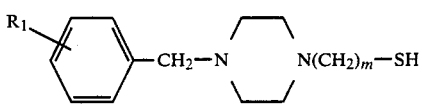

The hydrolysis can be performed by treatment of the isothiouronium salt with a base, such as sodium hydroxide, preferably with heating. Compounds of formula IV and their preparation are described in application Ser. No. 6/499,188, filed May 31, 1984, now abandoned and assigned to the instant assignee. The resulting thiol is oxidized in known manner by treatment with an oxidizing agent, such as iodine or hydrogen peroxide, to provide a compound of formula I wherein X is a dithio linkage. The oxidation can be carried out under a wide variety of conditions including basic conditions, preferably in an aqueous environment, with or without hydrogen peroxide, and at ambient or elevated temperatures.

In another method, a mercaptoalkanol of the formula $HO(CH_2)_m—SH$ (V) is oxidized in known manner such as by treatment with 30% hydrogen peroxide, to form a compound of formula VI:

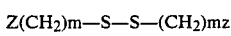

$$Z(CH_2)m—S—S—(CH_2)mz \quad VI$$

wherein m is as defined above and Z is hydroxyl. This intermediate can be converted in known manner to a compound of the above formula VI wherein Z is a reactive group capable of forming a carbon-nitrogen bond on reaction with an arylpiperazine of the formula VII:

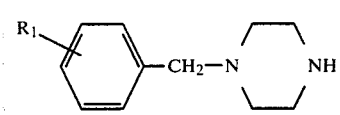

wherein $R_1$ is as described above, to provide a compound of formula I, wherein $R_1$, $R_2$, m and n are as described above, m is equal to n, and X is a dithio linkage. Suitable reactive groups include halogen or an activated ester group such as tosyl, a sulfuric acid ester, sulfonic acid ester or the like, preferably chlorine, bromine or tosyl. Suitable solvents include ethanol, dimethylsulfoxide or dimethylformamide in the presence of potassium hydroxide or triethylamine, optionally with heating.

The compound of formula I where X is thio can be made by treating a thiol of formula IV, wherein $R_1$ and m are as described above, with a compound of the formula II, wherein $R_1$, m and z are as described above. Suitable solvents are as described above. Treatment of this thio product with a mild oxidizing agent such as sodium meta-periodate provides a compound of formula I, wherein $R_1$, $R_2$, m, and n are as described above and X is sulfinyl. This can be performed using other mild oxidizing agents in suitable solvents such as water or inert organic solvents such as alcohol or acetic acid at or below room temperature.

Subsequent treatment of this sulfinyl product, or the thio precursor, with a stronger oxidizing agent, such as potassium permanganate, provides a sulfone of formula I, wherein $R_1$, $R_2$, m, and n are as described above and X is a sulfonyl group.

Conditions applied to the preparation of the sulfinyl are likewise appropriate for the preparation of the sulfonyl derivatives with the provision that stronger oxidizing agents and/or longer reaction times are employed.

Compounds of formula I wherein X is thio can also be prepared by treatment of compound of formula II with sodium sulfide in a suitable inert solvent such as an alcohol at ambient to solvent reflux temperatures. Elevated temperatures are preferred.

Investigators have determined the degree of histamine release from blood basophils as highly suggestive of the degree of allergic sensitivity of the cell donor patient. See Lichtenstein L.M. and Osler H.G., "Studies on the Mechanism of Hypersensitivity Phenomena. Histamine Release from Human Leucocytes by Ragweed Pollen Antigen", J. Exp. Med., 120:507(1964). This is generally discussed in Fudenberg H.H., et al (Eds.), *Basic & Clinical Immunology*. Lange Medical Publications, Los Altos, CA (1976) at pages 213–214 where histamine release from sensitized leucocytes (basophils) is characterized as a practical in vitro miniature allergic reaction which is used extensively as a test for allergy. In developing the present invention, the above procedure was adapted, inter alia, to determine the effect of compounds of the invention on inhibiting the histamine release induced by anti-IgE (basophil stabilization), with the procedural details and resulting data as reported below in Example 17.

For pharmaceutical purposes as antiallergic agents, the compounds of the present invention are administered topically to the skin or preferably to the mucosa of the eye, nose, or respiratory tract in conventional pharmaceutical compositions, that is compositions comprising an inert pharmaceutical carrier and an effective amount of the active ingredient.

For administration to the respiratory tract, the compounds can be administered as an aerosol or as a solution dispensed from a nebulizer, or as a microfine powder for insufflation, alone or in combination with an inert carrier such as lactose. Where appropriate, small amounts of other antiallergic and antiasthmatic bronchodilators, for example sympathomimetic amines such as isoprenaline, isoetharine, metaproterenol, salbutamol, phenylephrine, fenoterol and ephedrine; xanthine derivatives such as theophylline and aminophylline; and corticosteroids such as prednisolone and adrenal stimulants such as ACTH may be included.

For administration to the skin, the compounds can be administered as an ointment, cream, lotion, gel, or aerosol. Solutions for topical application to the nose can conveniently be administered by nasal sprays or drops. In addition, formulations for application to the eye can include drops, emulsions, or ointments.

Topical preparations for the nose and the eye can contain, in addition to the compounds of this invention, suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added can include benzalkonium chloride, thimerosal, chlorobutanol or phenylethyl alcohol. Topical preparations for the eye can also be prepared as ointments in a suitable inert base consisting of mineral oil, petrolatum, polyethylene glycols or lanolin derivatives, with or without microbial preservatives.

Preparations for the topical administration of the compounds of formula I for inhalation, or to the eye or nasal mucosa can preferably contain 0.005% (w/w) to about 1% of the active ingredient, depending upon the solubility of the particular compound and the desired pH of the solution.

Ointments for topical administration to the skin or the eye can preferably contain about 0.1% to about 5% (w/w) of the active ingredient.

The topical formulations containing the active ingredients can be adminstered as needed depending upon the nature and severity of the allergic disorder being treated. In general, the formulations can be applied topically one to four times per day.

Compounds of formula I can be employed in a conventional manner for the treatment of allergic disorders, for example asthma, rhinitis, conjunctivitis, hay fever, uriticaria and food allergies.

The present invention will now be illustrated, but is not intended to be limited, by the following examples.

EXAMPLE 1

1,1'-(Dithiodi-3,1-propanediyl)bis[4-(4-chlorobenzyl)piperazine]

First, 1-(4-chlorobenzyl)piperazine (20.0 g) is mixed with dimethyl sulfoxide (100 ml), potassium hydroxide (15.0 g) and 1-bromo-3-chloropropane (15.0 g) at room temperature for 3 hours. Water is added to the resulting solution, the reaction product is extracted with ether, dried (magnesium sulfate), and the salt is precipitated with ethereal hydrochloric acid to yield 25.1 g of 1-(4-chlorobenzyl)-4-(3-chloropropyl)piperazine dihydrochloride as a white crystalline solid.

Then, the 1-(4-chlorobenzyl-4-(3-chloropropyl)piperazine dihydrochloride (25.2 g) so-prepared is reacted with thiourea (6.0 g) and triethylamine (8.7 g) in reagent ethanol (200 ml).

The mixture is refluxed for 8 hours. After the addition of a solution of sodium hydroxide (5.0 g) in water (50 ml), the resulting mixture is refluxed for 4 additional hours. The ethanol is removed in vacuo, and water is added to the residue which is extracted with methylene chloride and dried (sodium sulfate). The salt is precipitated with ethereal hydrochloric acid to give 16.6 g of 3-[4-(4-chlorobenzyl)piperazine-1-yl]propanethiol dihydrochloride as an off-white crystalline solid, M.p. 257°-260° C.

Elemental Analysis:
Calculated: C, 47.13; H, 6.22; N, 7.85.
Found: C, 46.92; H, 6.24; N, 7.74.

EXAMPLE 2

1,1'-(Dithiodi-2,1-ethandediyl)bis[4-(4-chlorobenzyl)piperazine]

First, 30% hydrogen peroxide (168 g) is added dropwise (extremely exothermic reaction) to 2-mercaptoethanol while maintaining the temperature at 50°-60° C. After the addition is complete the mixture is allowed to stand for 2 hours and the water is removed in vacuo. Concentrated hydrochloric acid (950 ml) is added and the mixture heated in a steam bath for one and one-half hours. The aqueous layer is decanted and the organic layer washed with water, dried (sodium sulfate) and the product distilled in vacuo to give 211.4 g of bis(2-chloroethyl)disulfide.

Bis(2-chloroethyl)disulfide (80 g) is slowly added to a heated (80° C.) mixture of 4-chlorobenzylpiperazine (178 g), dimethylsulfoxide (500 ml), and potassium hydroxide (56 g). Fifteen minutes after the addition is complete, the mixture is poured over ice and the product extracted with ether, dried (sodium sulfate), and concentrated. The product is precipitated with ethereal hydrochloric acid to give 161.3 g of product. Recrystallization several times from water/acetone gives 1,1'-(dithiodi-2,1-ethanediyl)bis[4-(4-chlorobenzyl)piperazine]-tetrahydrochloride as a white crystalline solid, mp. 270°-273°

Elemental Analysis:
Calculated: C, 45.56; H, 5.88; N, 8.17.
Found: C, 45.27; H, 5.69; N, 8.09.

EXAMPLE 3

1,1'-(Dithiodi-2,1-ethanediyl)bis[4-(2-methylbenzyl)piperazine]

First, 2-chlorobromoethane (48 g) is added to a solution of 2-methylbenzylpiperazine (12 g) and triethylamine (32 g). The resulting mixture is refluxed for 30 minutes; water is then added and the product is extracted with ether, dried (magnesium sulfate) and concentrated in vacuo to give an oil, which is purified on a silica gel column (methylene chloride: methanol, 9:1). The resulting oil is dissolved in ether and the salt precipitated with ethereal hydrochloric acid to give 9.2 g of 1-(2-chloroethyl)-4-(2-methylbenzyl)piperazine dihydrochloride as colorless crystals.

A mixture of 1-(2-chloroethyl)-4-(2-methylbenzyl)-piperazine dihydrochloride (14 g), thiourea (6.5 g), triethylamine (8.7 g), and ethanol (200 ml) is refluxed for 6 hours and left to stir overnight at room temperature. A solution of sodium hydroxide (6 g) in water (50 ml) is added and the mixture refluxed an additional 4 hours.

The ethanol is removed in vacuo and water is added to the residue. The product is then extracted with methylene chloride, dried (sodium sulfate), and concentrated in vacuo to give an oil, which is purified on a silica gel column (ethyl acetate: ethanol: ammonium hydroxide, 50:5:1) and treated with ethereal hydrochloric acid to provide 6.4 g of the salt. Recrystallization from aqueous ethanol gives 1,1'-(dithiodi-2,1-ethanediyl)bis[4-(2-methylbenzyl) piperazine]tetrahydrochloride as a white crystalline solid, m.p. 249°–251° C.

Elemental Analysis:
Calculated: C, 52.17; H, 7.19; N, 8.69.
Found: C, 52.28; H, 7.36; N, 8.82.

EXAMPLE 4

{2-[4-(4-Chlorobenzyl)piperazin-1-yl]ethyl}{3-(4-(4-chlorobenzyl) piperazin-1-yl)propyl}sulfide A mixture of 3-[4-(4-chlorobenzyl)piperazine-1-yl]propanethiol dihydrochloride (2 g), sodium hydroxide (0.3 g), water (10 ml), and ethanol (100 ml) is refluxed for 15 minutes, and then a solution of 1-(2-chloroethyl)-4-(4-chlorobenzyl)piperazine (1.9 g) in ethanol (20 ml) is added. The resulting mixture is refluxed for 2 hours and the ethanol is removed in vacuo. Water is added to the residue and the product is extracted with methylene chloride, dried (magnesium sulfate), and concentrated. The resulting oil is purified on a silica gel column (methylene chloride: methanol, 9:1), and then dissolved in ether. The product is precipitated with ethereal hydrochloric acid and recrystallized from aqueous ethanol to provide 1.2 g of {2-[4-(4-chlorobenzyl)piperazin-1-yl]ethyl}{3-[4-(4-chlorobenzyl)piperazin-1-yl]propyl}sulfide tetrahydrochloride as colorless crystals, m.p. 292°–295° C.

Elemental Analysis:
Calculated: C, 48.59; H, 6.34; N, 8.39.
Found: C, 48.29; H, 6.17; N, 8.29.

EXAMPLE 5

1,1'-(Thio-3, 1-propanediyl) bis[4-(4-chlorobenzyl)piperazine]

A solution of 1-(3-chloropropyl)-4-(4-chlorobenzyl)-piperazine (10.0 g) in ethanol (60 ml) is added dropwise to a refluxing solution of sodium sulfide nonahydrate (8.4 g) in ethanol (150 ml). After the addition is complete, the mixture is refluxed for an additional 1½ hours and the solvent is removed in vacuo. Water is added to the residue and the product is extracted with methylene chloride, dried (magnesium sulfate) and concentrated. The resulting oil is dissolved in ether and the salt precipitated with ethereal hydrochloric acid and recrystallized from aqueous ethanol to provide 8.5 g of 1,1'-(thio-3,1-propanediyl) bis-[4-(4-chlorobenzyl) piperazine] tetrahydrochloride as a white crystalline solid, m.p. 288°–292° C.

Elemental Analysis
Calculated: C, 49.35; H, 6.51; N, 8.22.
Found: C, 49.34; H, 6.43; N, 8.09.

EXAMPLE 6

1,1'-(Sulfinyl-3,1-propanediyl) bis[4-(4-chlorobenzyl) piperazine]

A solution of sodium metaperiodate (1.95 g) in water (30 ml) is added dropwise to an ice cold mixture of 1,1'-(thio-3,1-propanediyl)-bis[4-(4-chlorobenzyl)piperazine (4.5 g) in methanol (75 ml). The mixture is allowed to stir 4 hours at 0° C., after which the methanol is removed in vacuo and water added to the residue. The product is extracted with methylene chloride, dried (magnesium sulfate), and concentrated to give an oil, which is dissolved in ether and the salt precipitated with ethereal hydrochloric acid. Recrystallization from aqueous ethanol provides 3.5 g of 1,1'-(sulfinyl-3,1-propanediyl) bis[4-(4-chlorobenzyl)piperazine] tetrahydrochloride as a white crystalline solid, m.p. 259°–263° C.

Elemental Analysis
Calculated: C, 48.22; H, 6.36; N, 8.03.
Found: C, 48.20; H, 6.23; N, 8.15.

EXAMPLE 7

1,1'-(Sulfonyl-3,1-propanediyl)bis[4-(4-chlorobenzyl)-piperazine]

A solution of potassium permanganate (0.5 g) in water (40 ml) is added dropwise to an ice cold solution of 1,1'-(sulfinyl-3,1-propanediyl)bis[4-(4-chlorobenzyl)-piperazine] tetrahydrochloride (1.5 g) in 50% acetic acid (50 ml). After the mixture is stirred for 1 hour, sulfur dioxide is bubbled into the mixture until the solution becomes decolorized. Water is then added and the product is extracted with methylene chloride, dried (magnesium sulfate), and concentrated. The resulting oil is dissolved in ether and the salt precipitated with ethereal hydrochloric acid and recrystallized from aqueous ethanol to provide 0.47 g of 1,1'-(sulfonyl-3,1-propanediyl) bis[4-(4-chlorobenzyl)piperazine] tetrahydrochloride as a white crystalline solid, m.p. 275°–278° C.

Elemental Analysis
Calculated: C, 46.64; H, 6.38; N, 7.76.
Found: C, 46.26; H, 6.03; N, 7.61.

EXAMPLE 8

1,1'-(Dithiodi-2,1-ethanediyl)bis[4-(4-cyanobenzyl)piperazine]

A mixture of 4-cyanobenzylpiperazine (4.0 g), bis(2-chloroethyl) disulfide (1.9 g), potassium hydroxide (5.0 g), and dimethylsulfoxide (50 ml) is heated at 80° C. until the solution turns pink in color. The heat is then removed and the reaction mixture allowed to stir overnight at room temperature. The solution is diluted with water, and the product extracted with ether, dried, and concentrated to give 4.4 g of an oil, which is purified on a silica gel column (methylene chloride: methanol, 98:2). The resulting light brown oil is dissolved in ether and the salt precipitated with ethereal hydrochloric acid to give, after recrystallization from aqueous ethanol, 1,1'-(dithiodi-2,1-ethanediyl)bis[4-(4-cyanobenzyl)-piperazine] tetrahydrochloride as a white crystalline solid, m.p. 272°–275° C.

Elemental Analysis
Calculated: C, 50.45; H, 6.04; N, 12.60.
Found: C, 50.34; H, 6.08; N, 12.49.

EXAMPLE 9

1,1'-(Dithiodi-3,1-propanediyl)bis[4-benzylpiperizine)

A solution of iodine (4.8 g) in acetone is added dropwise to a solution of 3-(4-benzylpiperazin-1-yl)propanethiol (9.7 g), sodium hydroxide (4.8 g), and acetone/water (1:2), and the resulting mixture allowed to stir at room temperature overnight. The acetone is removed in vacuo and the product extracted with ether, dried, and concentrated to give an oil which is purified on a silica gel column (methylene chloride: methanol, 9:1). The resulting oil 4.1 g is dissolved in ethanol and the salt precipitated with ethereal hydrochloric acid to give, after recrystallization from aqueous ethanol, 1,1'-(dithiodi-3,1-propanediyl)bis(4-benzylpiperazine) tetrahydrochloride as a white crystalline solid, m.p. 273°–276° C.

Elemental Analysis
Calculated: C, 52.16; H, 7.19; N, 8.69.
Found: C, 52.17; H, 7.09; N, 8.61.

EXAMPLE 10

1,1'-(Dithiodi-3,1-propanediyl)bis[4-(4-chlorophenethyl)piperazine]

The procedure described in Example 9 is followed using 3-[4-(4-chlorophenethyl)piperazin-1-yl]propanethiol (1.7 g), sodium hydroxide (0.7 g), and iodine (0.9 g). Workup as described above provides 1.3 g of the free base, which is treated with ethereal hydrochloric acid and recrystallized from water/acetone and then from ethanol/water to give 1,1'-(dithiodi-3,1-propanediyl)-bis [4-(4-chlorophenethyl)piperazine] tetrahydrochloride as a white crystalline solid, m.p. 290°–300° C.

Elemental Analysis
Calculated: C, 48.58; H, 6.52; N, 7.55.
Found: C, 48.28; H, 6.48; N, 7.41.

EXAMPLE 11

1,1'-(Dithiodi-3,1-propanediyl)bis[4-(4-chlorobenzyl)-homopiperizine]

A mixture of 3-[4-(4-chlorobenzyl)homopiperazin-1-yl]-propanethiol (4.0 g) and 2N sodium hydroxide (50 ml) is stirred at room temperature for 8 days. The product is extracted with ether, dried, and concentrated to give a yellow oil, which is purified on a silica gel column (methylene chloride:methanol, 95:5). The resulting yellow oil (1.5 g) is dissolved in ether and the salt precipitated with ethereal hydrochloric acid. Recrystallization from ethanol provided 1,1'-(dithiodi-3,1-propanediyl)bis[4-(4-chlorobenzyl) homopiperizine] tetrahydrochloride as a white crystalline solid, m.p. >170° (dec.).

Elemental Analysis
Calculated: C, 46.88; H, 6.68; N, 7.28.
Found: C, 46.72; H, 6.83; N, 7.17.

Example 12

1,1'-(Dithiodi-2,1-ethanediyl)bis[4-(4-methylbenzyl)piperazine]

A solution of bis(2-chloroethyl)disulfide (2.9 g) in dimethylsulfoxide (5 ml) is added dropwise to a warmed mixture of (4-methylbenzyl)piperazine (5.7 g), potassium hydroxide (5.0 g), and dimethylsulfoxide (55 ml). The resulting mixture is stirred an additional 4 hours after which it is poured over ice/water and the product extracted with methylene chloride, dried and concentrated. The resulting oil (6.5 g) is purified on a silica gel column (methylene chloride:methanol, 95:5), and the salt precipitated with ethereal hydrochloric acid to provide, after recrystallization from ethanol/water, 1,1'-(dithiodi-2,1-ethanediyl)bis[4-(4-methylbenzyl)piperazine] tetrahydrochloride as a white crystalline solid, m.p. 280°–282° C.

Elemental Analysis
Calculated: C,52.16; H,7.19; N,8.69.
Found: C,51.87; H,7.37; N,8.63.

Example 13

1,1'-(Dithiodi-2,1-ethanediyl)bis{4-[3-(4-chlorophenyl)-propyl]piperazine}

The procedure described in Example 12 is followed using 1[3-(4-chlorophenyl)propyl]-piperazine (4.8 g), bis(2-chloroethyl) disulfide (1.9 g), potassium hydroxide (5.0 g), and dimethylsulfoxide (50 ml). Workup as described in Example 12 provides an oil which is purified on a silica gel column (methylene chloride:methanol, 9:1). The resulting oil (1.5 g) is precipitated with ethereal hydrochloric acid and recrystallized from water/ethanol to give 1,1'-(dithiodi-2, 1-ethanediyl)bis{4-[3-(4-chlorophenyl)propyl]piperazine} tetrahydrochloride as a white crystalline solid, m.p. 284°–286° C.

Elemental Analysis
Calculated: C,47.43; H,6.63; N,7.37.
Found: C,47.44; H,6.76; N,7.30.

Example 14

1,1'-(Dithiodi-2,1-ethanediyl)bis{4-[4-methylthio)benzyl])piperazine}

A solution of thionyl chloride (47.6 g) in methylene chloride is slowly added to a solution of 4-(methylthio)-benzyl alcohol (50.0 g) in pyridine (37.2 g) such that the temperature never exceeds 25° C. After the addition is complete the mixture is stirred an additional 2 hours at room temperature, then washed with water, dried, and the solvents removed. The resulting red oil is mixed with hexane which is decanted and evaporated to give 49.6 g of 4-(methylthio)benzyl chloride as a yellow oil, suitable for use in the reaction described next below.

A mixture of 4-(methylthio)benzyl chloride (28.6 g), 1-(2-hydroxyethyl)piperazine (21.6 g), triethylamine (16.8 g), and ethanol (250 ml) is stirred at room temperature for 5 hours. The ethanol is then removed in vacuo and water added to the residue. The product is extracted with ether, dried, and the ether evaporated to give 31.6 g of 1-(2-hydroxyethyl)-4-[4-(methylthio)benzyl] piperazine as an orange oil, suitable for use in the next reaction.

A solution of thionyl chloride (21.2 g) in methylene chloride (100 ml) is added to an ice cold solution of 1-(2-hydroxyethyl)-4-[4-(methylthio)benzyl] piperazine (31.6 g) in methylene chloride. (250 ml). Triethylamine (12.0 g) in methylene chloride (100 ml) is then added and the resulting mixture refluxed for 1 hour and then allowed to stir overnight at room temperature. The mixture is then washed with water, basified, and the product extracted with ether. The ether solution is dried and concentrated to give an oil (21.6 g) which is purified on silica gel column (methylene chloride:methanol, 9:1) to provide 1-(2-chloroethyl)-4-[4-(methylthio)-benzyl] piperazine as an oil.

Thiourea (2.0 g) is added to a solution of 1-(2-chloroethyl)-4-[4-(methylthio)benzyl]piperazine (6.7 g) in ethanol (200 ml), and the resulting mixture refluxed for 30 minutes. The solution is then diluted with additional ethanol (150 ml) and cooled in an ice bath. A solution of sodium hydroxide (2.8 g) in water (10 ml) is slowly added followed by iodine (3.3 g) in 12 ml of ethanol/acetone (1:2). The reaction mixture is diluted with water, and the product extracted with ether, dried, and the salt precipitated with ethereal hydrochloric acid to give 6.85 g of product. Several recrystallizations from water/ethanol provide 1,1'-(dithiodi-2,1-ethanediyl)

bis{4-[4-(methylthio)benzyl]piperazine} tetrahydrochloride as a white crystalline solid, m.p. 274°–276° C.

Elemental Analysis
Calculated: C, 47.44; H, 6.54; N, 7.90.
Found: C, 47.56; H, 6.55; N, 7.96.

EXAMPLE 15

1,1'-(Dithiodi-2,1-ethanediyl)bis[4-(3-chlorobenzyl)piperazine]

The procedure described in Example 14 is followed, starting from the commercially available 3-chlorobenzylchloride. The final step is effected as follows. A mixture of 1-(2-chloroethyl)-4-(3-chlorobenzyl)piperazine (24.0 g), thiourea (10.0 g), and ethanol (200 ml) was refluxed for 45 minutes. The mixture was then cooled in an ice bath in a solution of sodium hydroxide (10.6 g) in water (50 ml) which is added dropwise. When the addition is complete a solution of iodine (13.4 g) in 100 ml of ethanol/acetone (1/1) is added dropwise to the cooled solution, which is stirred for an additional 30 minutes at room temperature. The ethanol is removed in vacuo and salt water added to the residue. The product is extracted with ether, dried, and concentrated to give an oil which is purified on silica gel column (methylene chloride: methanol. 95:5) and the salt is precipitated with ethereal hydrochloric acid to give 10.1 g (33% yield). Recrystallization from water/ethanol provided 1,1'-(dithiodi-2,1-ethanediyl)bis[4-(3-chlorobenzyl)piperazine] tetrahydrochloride as a white crystalline solid, m.p. 275°–282° C.

Elemental Analysis
Calculated: C 45.56; H 5.88; N 8.17.
Found: C 45.53; H 5.99; N 7.98

EXAMPLE 16

1,1'-(Dithiodi-2,1-ethanediyl)bis[4-(4-bromobenzyl)piperazine]

The procedure described in Example 15 is followed using 1-(2-chloroethyl)-4-(4-bromobenzyl)piperazine (20 g) and thiourea (7.2 g) in ethanol (200 ml), followed by sodium hydroxide (7.6 g) in water (50 ml), and then by iodine (9.6 g) in ethanol/acetone (100 ml) (1:1). Workup as described above provided 9.6 g of product, which is recrystallized from water/ethanol to give 1,1'-(dithiodi-2, 1-ethanediyl)bis-[4-(4-bromobenzyl)piperazine] tetrahydrochloride hemihydrate as a white crystalline solid, m.p. >275° (dec.).

Elemental Analysis
Calculated: C 39.86; H 5.27; N 7.15.
Found: C 39.67; H 5.10; N 7.05

EXAMPLE 17

In the experiments reported by this example compounds in accordance with the invention are evaluated to determine their ability to inhibit the IgE-mediated release of histamine from sensitized peripheral leucocytes (basophils).

HUMAN BASOPHIL ASSAY

Separation of leukocytes is accomplished by a modification of the method of L. Lichtenstein and A. Osler, *J. Exp. Med.* 120: 507 (1964). Heparinized human blood (80–100 ml) is mixed with 20 ml of saline (0.2%) containing 0.6 g of dextrose and 1.2 g of dextran in propylene centrifuge tubes. The mixture is kept at ambient temperature for 60–90 minutes to allow the separation of erythrocytes from the platelet-leukocyte-rich supernate. The supernate is removed and centrifuged for 8 minutes at $10 \times g$ in the cold. The leukocyte pellet is washed twice with Tris buffer and finally suspended in 150–180 ml Tris-ACM buffer at $1-2 \times 10^6$ cells/ml.

The reaction is carried out in $12 \times 75$ mm plastic tubes at a total volume of 1.23 ml. The reaction medium includes 0.05 ml rabbit anti-human IgE, 0.2 ml of the test compound in Tris-ACM buffer at concentrations ranging from 10–1000 $\mu M$, and 1.0 ml of the leukocyte suspension. The reaction mixture is incubated in a 37° C. shaking water bath for 60 minutes. Upon completion of the reaction, the tubes are centrifuged and the supernatants collected. The protein is removed from the supernatants by precipitation with 0.2 ml of 8% perchloric acid.

Histamine release is measured by the automated fluorometric method of W Siraganian and W. Hook in Chapter 108, pages 808–821 of the *Manual of Clinical Immunology*, 2nd Edition, edited by R. Rose and H. Friedman, published by the American Society for Microbiology, Washington, D.C., 1980. Percent inhibition is calculated as follows:

$$\frac{(\text{Control} - \text{blank}) - (\text{Test sample} - \text{blank})}{(\text{Control} - \text{blank})} \times 100$$

The concentration which causes a 50 percent inhibition ($IC_{50}$) of histamine release is interpolated from a plot of percent inhibition versus the logarithm of drug concentration.

The results of the testing of compounds of formula I for the inhibition of histamine release from human leukocytes (basophils) according to the above procedure are shown in Table 1 below:

TABLE 1

| IN VITRO INHIBITION OF HISTAMINE RELEASE $IC_{50}$ ($\mu M$) | |
|---|---|
| TEST COMPOUND (Example No.) | $IC_{50}$ ($\mu M$) |
| 1 | 2.0 |
| 2 | 2.4 |
| 3 | 15.0 |
| 4 | 2.4 |
| 5 | 1.9 |
| 6 | 5.6 |
| 7 | 3.4 |
| 8 | 28.0 |
| 9 | 13.7 |
| 10 | >1000 |
| 11 | >1000 |
| 12 | 4.7 |
| 13 | >1000 |

The results reported in Table 1 clearly demonstrate that the compounds in accordance with the invention effectively inhibit the release of histamine in human basophils, unlike the absence of observed activity with compounds such as those described in Examples 10, 11 and 13 herein.

EXAMPLE 18

The experiments reported here further evaluate the compound prepared as described in Example 2 in accordance with the protocol described in Example 17.

Testing of 1,1-(dithiodi-2,1-ethanediyl)bis[4-(4-chlorobenzyl)piperazine] tetrahydrochloride over a range of concentrations up to the limits of its solubility provides in this instance an $IC_{50}$ of $3.7 \times 10^{-6} M$.

Further repetition of such testing gives IC$_{50}$ of 5.29×10$^{-6}$M

EXAMPLE 19

The previously described assay is also performed by an identical protocol except that basophils are activated for the release of histamine by a non-immunological ionophore A-23187 available from Eli Lilly & Co. (Indianapolis, IN). The assay over a 1000-fold test dosage range gives an IC$_{50}$ of 2.67×10$^{-6}$M.

EXAMPLES 20

Topical solution (ophthalmic or nasal)

The solution composition is compounded from the following ingredients:

| | |
|---|---|
| 1,1'-(dithiodi-2,1-ethanediyl)bis[4-(4-chlorobenzyl)piperazine] tetrahydrochloride | 0.4 g |
| glycerin | 1.0 g |
| benzalkonium chloride | 0.01 g |
| phosphate buffer (pH 5.5). q.s.ad | 100.0 ml |

The ingredients are dissolved in the conventional manner to form an aqueous solution. The solution is appropriately filtered, with the ophthalmic solution requiring sterile filtration. Each ml of the solution contains 4.0 mg of the active ingredient.

EXAMPLE 21

Ointment

The ointment composition utilizes the following base compounded in a conventional manner.

| | |
|---|---|
| 1,1'-(dithiodi-2,1-ethanediyl)bis[4-(4-bromobenzyl)peperazine] tetrahydrochloride hemihydrate | 3.8 g |
| white petrolatum | 70.7 g |
| mineral oil | 23.6 g |
| white wax | 1.9 g |

The active ingredient is uniformly incorporated into the base at the required concentration.

EXAMPLE 22

Inhalation aerosol

The aerosol composition is prepared from the following ingredients:

| | |
|---|---|
| 1,1'-(dithiodi-2,1-ethanediyl)bis[4-(4-cyanobenzyl)piperzaine] tetrahydrochloride | 1.00 parts |
| Soybean lecithin | 0.20 parts |
| Propellant gas mixture (Freon 11, 12 and 14) q.s.ad | 100.00 parts |

The ingredients are compounded in conventional manner, and the composition is filled into aerosol containers with a metering valve which releases 0.5 to 2.0 mg of active ingredient per actuation of the valve.

Any one of the other compounds embraced by formula I or a nontoxic, pharmaceutically acceptable addition salt thereof may be substituted for the particular active ingredient in Examples 20 through 22. Likewise, the amount of active ingredient in these illustrative examples may be varied to achieve the desired dosage unit range, and the amounts and nature of the inert pharmaceutical carrier ingredient may be varied to meet particular requirements.

Although the invention has been described with particularity, one skilled in the field can resort to numerous changes in the details, combinations and arrangements of elements without departing from the scope of the invention.

What is claimed is:

1. A compound of the formula:

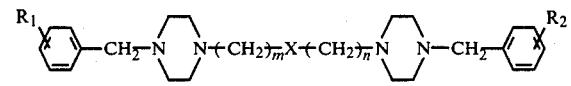

wherein

R$_1$ and R$_2$ are each independently hydrogen, lower alkyl, halogen, nitrile or methylthio; m and n are each independently 2 or 3; and X is dithio or thio, and nontoxic, pharmaceutically acceptable addition salts thereof.

2. A compound of claim 1 wherein R$_1$ and R$_2$ are each independently a halogen selected from chlorine or bromine.

3. A compound of claim 1 wherein R$_1$ and R$_2$ are both in the para position, and nontoxic, pharmaceutically acceptable addition salts thereof.

4. A compound of claim 1 which is 1,1'-(Dithiodi-3,1-propanediyl)bis[4-(4-chlorobenzyl)piperazine] and nontoxic, pharmaceutically acceptable addition salts thereof.

5. A compound of claim 1 which is 1,1'-(Dithiodi-2,1-ethanediyl)bis[4-(4-chlorobenzyl)piperazine] and nontoxic, pharmaceutically acceptable addition salts thereof.

6. A compound of claim 1 which is 1,1'-(Dithiodi-2,1-ethanediyl)bis[4-(2-methylbenzyl)piperazine] and nontoxic, pharmaceutically acceptable addition salts thereof.

7. A compound of claim 1 which is {2[4-(4-chlorobenzyl)piperazine-1-yl]ethyl}{3-[4-(4-chlorobenzyl)piperazin-1-yl]propyl}sulfide and nontoxic, pharmaceutically acceptable addition salts thereof.

8. A compound of claim 1 which is 1,1'-(Thio-3,1-propanediyl)bis[4-(4-chlorobenzyl)piperazine] and nontoxic, pharmaceutically acceptable addition salts thereof.

9. A compound of claim 1 which is 1,1'-(Sulfinyl-3,1-propanediyl)bis[4-(4-chlorobenzyl)piperazine] and nontoxic, pharmaceutically acceptable addition salts thereof.

10. A compound of claim 1 which is 1,1'-(Dithiodi-2,1-ethanediyl)bis[4-(4-cyanobenzyl)piperazine] and nontoxic, pharmaceutically acceptable addition salts thereof.

11. A compound of claim 1 which is 1,1'-(Dithiodi-3,1-propanediyl)bis[4-benzylpiperizine) and nontoxic, pharmaceutically acceptable addition salts thereof.

12. A compound of claim 1 which is 1,1'-(Dithiodi-2,1-ethanediyl)bis[4-(4-methylbenzyl)piperazine] and nontoxic, pharmaceutically acceptable addition salts thereof.

13. A compound of claim 1 which is 1,1'-(Dithiodi-2,1-ethanediyl)bis{4-[4-(methylthio)benzyl]piperazine} and nontoxic, pharmaceutically acceptable addition salts thereof.

14. A compound of claim 1 which is 1,1'-(Dithiodi-2,1-ethanediyl)bis[4-(3-chlorobenzyl)piperazine] and nontoxic, pharmaceutically acceptable addition salts thereof.

15. A compound of claim 1 which is 1,1'-(Dithiodi-2,1-ethanediyl)bis[4-(4-bromobenzyl)piperazine] and nontoxic, pharmaceutically acceptable addition salts thereof.

16. A topical antiallergic or antiinflammatory composition comprising an effective antiallergic or antiinflammatory amount of a compound of claim 1 in combination with a nontoxic, pharmaceutically acceptable carrier.

17. A method of suppressing allergic reactions or inflammation in a warm-blooded animal in need thereof, which comprises topically administering to said animal an effective antiallergic or antiinflammatory amount of a compound of claim 1.

18. A method of suppressing allergic reactions in a warm-blooded animal in need thereof, which comprises topically administering to said animal an effective antiallergic amount of a compound of claim 1.

* * * * *